US011779299B2

(12) United States Patent
Nakayama et al.

(10) Patent No.: US 11,779,299 B2
(45) Date of Patent: Oct. 10, 2023

(54) CONTROL DEVICE, CONTROL METHOD, AND CONTROL PROGRAM

(71) Applicant: FUJIFILM CORPORATION, Tokyo (JP)

(72) Inventors: Hiroki Nakayama, Kanagawa (JP); Tomoki Inoue, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 51 days.

(21) Appl. No.: 17/485,527

(22) Filed: Sep. 27, 2021

(65) Prior Publication Data

US 2022/0096039 A1  Mar. 31, 2022

(30) Foreign Application Priority Data

Sep. 28, 2020  (JP) .................................. 2020-162698

(51) Int. Cl.
*A61B 6/00* (2006.01)
*A61B 6/04* (2006.01)
*A61B 6/02* (2006.01)

(52) U.S. Cl.
CPC .............. *A61B 6/542* (2013.01); *A61B 6/025* (2013.01); *A61B 6/0414* (2013.01);
(Continued)

(58) Field of Classification Search
CPC ......... A61B 6/025; A61B 6/481; A61B 6/482; A61B 6/502
See application file for complete search history.

(56) References Cited

U.S. PATENT DOCUMENTS

| 2012/0238870 | A1* | 9/2012 | Smith .................... A61B 6/466 600/431 |
| 2016/0235380 | A1 | 8/2016 | Smith et al. |
| 2020/0146645 | A1 | 5/2020 | Nakayama |

FOREIGN PATENT DOCUMENTS

| JP | 2009-183373 A | 8/2009 |
| JP | 2013-198736 A | 10/2013 |

(Continued)

OTHER PUBLICATIONS

English language translation of the following: Office action dated May 16, 2023 from the JPO in a Japanese patent application No. 2020-162698 corresponding to the instant patent application. This office action translation is submitted now in order to supplement the understanding of the cited references which are being disclosed in the instant Information Disclosure Statement.

*Primary Examiner* — Dani Fox
(74) *Attorney, Agent, or Firm* — SOLARIS Intellectual Property Group, PLLC

(57) ABSTRACT

A control device including: wherein the processor controls a mammography apparatus that a breast, with radiation from a radiation source to capture a radiographic image of the breast such that normal imaging which emits the radiation with first energy from an irradiation position where an irradiation angle is 0 degrees to capture a normal radiographic image and tomosynthesis imaging which emits the radiation with either the first energy or second energy higher than the first energy at each of a plurality of irradiation positions having different irradiation angles and emits the radiation with the second energy at the irradiation position where the irradiation angle is 0 degrees to capture a plurality of low-energy projection images and a plurality of high-energy projection images are performed in a state in which the breast is compressed by the compression member.

11 Claims, 10 Drawing Sheets

(52) U.S. Cl.
 CPC .......... *A61B 6/4291* (2013.01); *A61B 6/4452* (2013.01); *A61B 6/481* (2013.01); *A61B 6/482* (2013.01); *A61B 6/502* (2013.01)

(56) References Cited

FOREIGN PATENT DOCUMENTS

| | | |
|---|---|---|
| JP | 2014-507250 A | 3/2014 |
| JP | 2019-069232 A | 5/2019 |
| WO | 2012/122399 A1 | 9/2012 |
| WO | 2019/017442 A1 | 1/2019 |

* cited by examiner

CONTROL DEVICE, CONTROL METHOD, AND CONTROL PROGRAM

CROSS-REFERENCE TO RELATED APPLICATION

The present application claims priority under 35 U.S.C. § 119 to Japanese Patent Application No. 2020-162698 filed on Sep. 28, 2020. The above application is hereby expressly incorporated by reference, in its entirety, into the present application.

BACKGROUND

Technical Field

The present disclosure relates to a control device, a control method, and a control program.

Description of the Related Art

Contrast imaging which irradiates an object into which a contrast medium is injected with radiation having different energy levels to capture a low-energy image and a high-energy image is performed to generate a difference image indicating a difference between the high-energy image and the low-energy image. The generated difference image is an image in which the body tissues of the object have been removed and the contrast medium is clearly shown.

In addition, so-called tomosynthesis imaging which sequentially emits radiation at each of a plurality of irradiation positions having different irradiation angles and captures a plurality of projection images with a radiation detector at each irradiation position is known as a method capturing a radiographic image. JP2014-507250A discloses a mammography apparatus that can perform contrast imaging and tomosynthesis imaging.

SUMMARY

However, in the contrast imaging, it is desirable to perform normal imaging which emits radiation from an irradiation position where the irradiation angle is 0 degrees to capture an image and tomosynthesis imaging in a state in which the breast is compressed in order to capture the images of the mammary glands or the like in the same manner. Further, in a case in which the normal imaging and the tomosynthesis imaging are performed in a state in which the breast is compressed, it is desirable to reduce the overall time of the contrast imaging. However, for example, in the technique disclosed in JP2014-507250A, in a case in which the normal imaging and the tomosynthesis imaging are continuously performed as the contrast imaging, the overall time of the contrast imaging may be relatively long.

The present disclosure has been made in view of the above-mentioned problems, and an object of the present disclosure is to provide a control device, a control method, and a control program that can reduce the overall time of contrast imaging in which normal imaging and tomosynthesis imaging are continuously performed.

In order to achieve the above object, according to a first aspect of the present disclosure, there is provided a control device comprising at least one processor. The processor controls a mammography apparatus that irradiates a breast, into which a contrast medium is injected and which is compressed by a compression member, with radiation from a radiation source to capture a radiographic image of the breast such that normal imaging which emits the radiation with first energy from an irradiation position where an irradiation angle is 0 degrees to capture a normal radiographic image and tomosynthesis imaging which emits the radiation with either the first energy or second energy higher than the first energy at each of a plurality of irradiation positions having different irradiation angles and emits the radiation with the second energy at the irradiation position where the irradiation angle is 0 degrees to capture a plurality of low-energy projection images based on the radiation with the first energy and a plurality of high-energy projection images based on the radiation with the second energy are performed in a state in which the breast is compressed by the compression member.

According to a second aspect of the present disclosure, in the control device according to the first aspect, the processor may acquire the normal radiographic image, the plurality of low-energy projection images, and the plurality of high-energy projection images, generate a difference image indicating a difference between the high-energy projection image in a case in which the irradiation angle is 0 degrees among the plurality of high-energy projection images and the normal radiographic image, and generate tomographic difference images indicating differences between high-energy tomographic images generated by reconstructing the plurality of high-energy projection images and low-energy tomographic images generated by reconstructing the plurality of low-energy projection images.

According to a third aspect of the present disclosure, in the control device according to the first aspect, the processor may acquire the normal radiographic image, the plurality of low-energy projection images, and the plurality of high-energy projection images, generate a difference image indicating a difference between the high-energy projection image in a case in which the irradiation angle is 0 degrees among the plurality of high-energy projection images and the normal radiographic image, and generate tomographic difference images indicating differences between high-energy tomographic images generated by reconstructing the plurality of high-energy projection images and low-energy tomographic images generated by reconstructing the normal radiographic image and the plurality of low-energy projection images.

According to a fourth aspect of the present disclosure, in the control device according to the first aspect, a sum of the number of times the low-energy projection image is captured and the number of times the high-energy projection image is captured may be an odd number.

According to a fifth aspect of the present disclosure, in the control device according to the first aspect, the number of times the low-energy projection image is captured may be equal to the number of times the high-energy projection image is captured.

According to a sixth aspect of the present disclosure, in the control device according to the first aspect, the processor may perform control such that a dose of the radiation emitted from the irradiation position where the irradiation angle is 0 degrees in the tomosynthesis imaging is higher than a dose of the radiation emitted from the irradiation positions having other irradiation angles.

According to a seventh aspect of the present disclosure, in the control device according to the first aspect, the processor may perform control such that the normal imaging is performed before the tomosynthesis imaging.

According to an eighth aspect of the present disclosure, in the control device according to the first aspect, the irradiation position where the irradiation angle is 0 degrees may be an irradiation position along a normal direction to an imaging table on which the breast is positioned.

According to a ninth aspect of the present disclosure, in the control device according to the first aspect, the mammography apparatus may comprise a grid in which a transmission portion that transmits the radiation and an absorption portion that absorbs the radiation are alternately arranged in a direction intersecting a movement direction in which the radiation source emitting the radiation is moved in the tomosynthesis imaging.

Further, in order to achieve the above object, according to a tenth aspect of the present disclosure, there is provided a control method comprising: controlling a mammography apparatus that irradiates a breast, into which a contrast medium is injected and which is compressed by a compression member, with radiation from a radiation source to capture a radiographic image of the breast such that normal imaging which emits the radiation with first energy from an irradiation position where an irradiation angle is 0 degrees to capture a normal radiographic image and tomosynthesis imaging which emits the radiation with either the first energy or second energy higher than the first energy at each of a plurality of irradiation positions having different irradiation angles and emits the radiation with the second energy at the irradiation position where the irradiation angle is 0 degrees to capture a plurality of low-energy projection images based on the radiation with the first energy and a plurality of high-energy projection images based on the radiation with the second energy are performed in a state in which the breast is compressed by the compression member.

Further, in order to achieve the above object, according to an eleventh aspect of the present disclosure, there is provided a non-transitory computer-readable storage medium storing a control program that causes a computer to perform a process of: controlling a mammography apparatus that irradiates a breast, into which a contrast medium is injected and which is compressed by a compression member, with radiation from a radiation source to capture a radiographic image of the breast such that normal imaging which emits the radiation with first energy from an irradiation position where an irradiation angle is 0 degrees to capture a normal radiographic image and tomosynthesis imaging which emits the radiation with either the first energy or second energy higher than the first energy at each of a plurality of irradiation positions having different irradiation angles and emits the radiation with the second energy at the irradiation position where the irradiation angle is 0 degrees to capture a plurality of low-energy projection images based on the radiation with the first energy and a plurality of high-energy projection images based on the radiation with the second energy are performed in a state in which the breast is compressed by the compression member.

According to the present disclosure, it is possible to reduce the overall time of contrast imaging in which normal imaging and tomosynthesis imaging are continuously performed.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the present disclosure will be described in detail with reference to the drawings. In addition, each of the embodiments does not limit the present disclosure.

Figure 1:
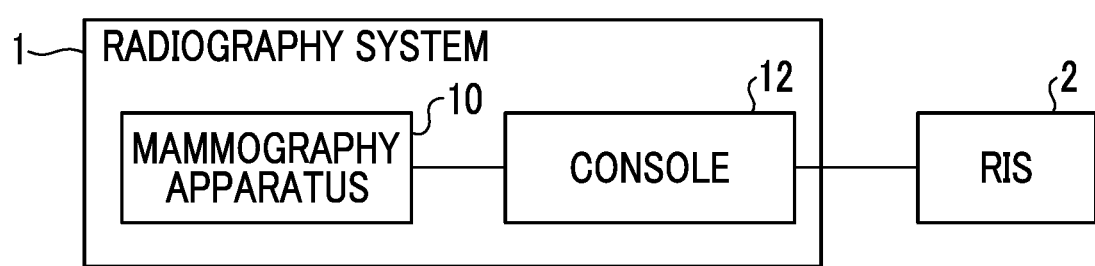
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. Further, the console 12 according to this embodiment is an example of a control device according to the present disclosure.

Figure 2A:
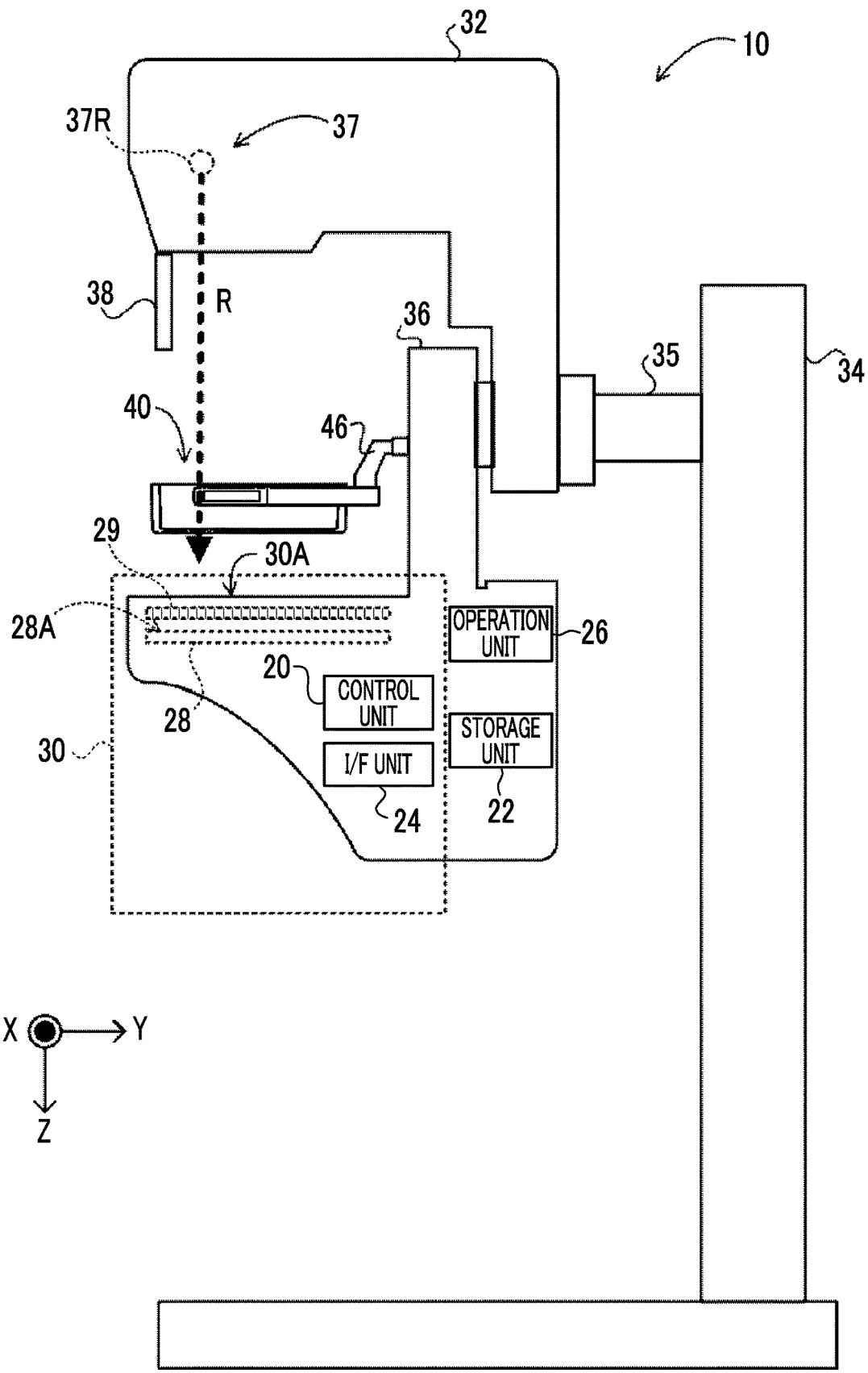
FIG. 2A is a side view illustrating an example of the outward appearance of a mammography apparatus according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

Further, the mammography apparatus 10 according to this embodiment performs two types of imaging, that is, so-called contrast imaging that is performed in a state in which a contrast medium is injected into the breast of the subject and general imaging that is performed without using the contrast medium. In addition, in this embodiment, imaging that is performed in a state in which the contrast medium injected into the breast of the subject is referred to as "contrast imaging", and imaging other than the contrast imaging is referred to as "general imaging". Furthermore, the mammography apparatus 10 according to this embodiment has a function of performing normal imaging that is performed at an irradiation position where a radiation source 37R is disposed along a direction normal to a detection surface 28A of a radiation detector, that is, an irradiation angle is 0 degrees and so-called tomosynthesis imaging that is performed while the radiation source 37R is moved to each of a plurality of irradiation positions. In addition, the mammography apparatus 10 can perform both the contrast imaging and the general imaging in both the normal imaging and the tomosynthesis imaging.

As illustrated in FIG. 2A, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, an operation unit 26 is provided as a plurality of switches in, for example, the imaging table 30 of the mammography apparatus 10. Further, the operation unit 26 may be provided as a touch panel switch or may be provided as a foot switch that is operated by the feet of the user such as a doctor or a radiology technician.

The radiation detector 28 detects the radiation R transmitted through the breast which is an object. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by the user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

Figure 2B:
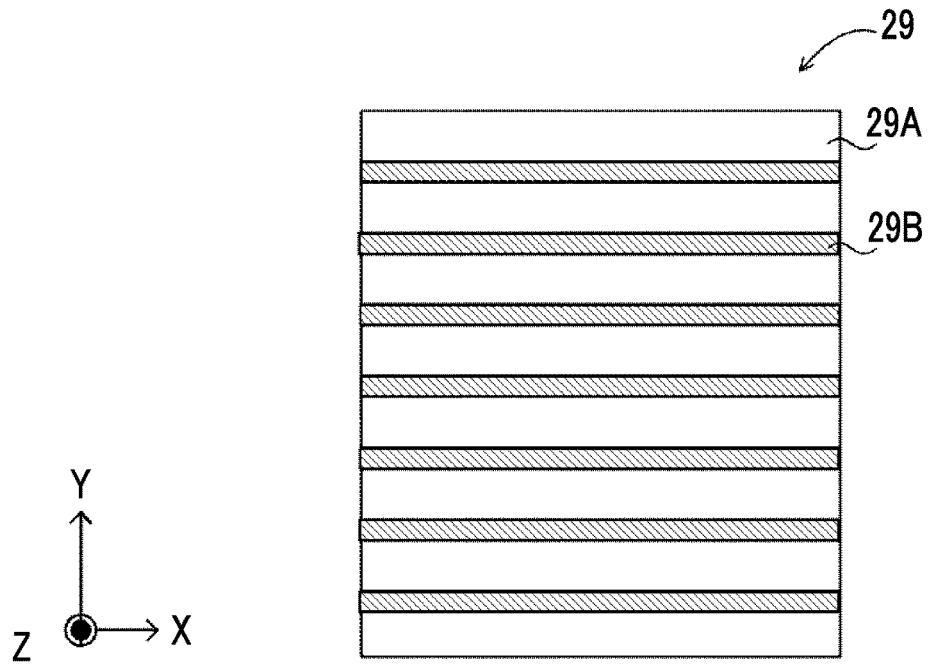
FIG. 2B is a plan view illustrating an example of a grid according to the embodiment as viewed from a radiation source.

Further, a grid 29 that removes scattered rays caused by the radiation transmitted through the breast is disposed in the imaging table 30. Specifically, as illustrated in FIG. 2A, the grid 29 is disposed between the radiation detector 28 and the imaging surface 30A of the imaging table 30. FIG. 2B is a plan view illustrating an example of the grid 29 according to this embodiment as viewed from the radiation source 37R.

As illustrated in FIG. 2B, the grid 29 comprises a transmission portion 29A that transmits the radiation R and an absorption portion 29B that absorbs the radiation. The transmission portion 29A and the absorption portion 29B are disposed in the imaging table 30 so as to extend in the left-right direction of the subject positioned on the imaging table 30. As illustrated in FIG. 2B, in the grid 29, the transmission portion 29A and the absorption portion 29B are alternately arranged in a direction (the front-rear direction of the subject) orthogonal to the left-right direction. In the mammography apparatus 10 according to this embodiment, in a case in which the tomosynthesis imaging is performed, the radiation source 37R of a radiation emitting unit 37 is moved in the left-right direction of the subject positioned on the imaging table 30, which will be described below. That is, in the grid 29 according to this embodiment, the transmission portion 29A and the absorption portion 29B are alternately arranged in a direction intersecting a movement direction M in which the radiation source 37R is moved.

An example of the material forming the absorption portion 29B is a lead thin film. Further, examples of the material forming the transmission portion 29A include aluminum, paper, and carbon fiber. As a tube voltage of the radiation source 37R becomes higher, the number of scattered rays tends to become larger. In addition, as a grid ratio becomes higher, it is more effective to reduce the scattered rays. Therefore, the grid ratio of the grid 29 is determined according to, for example, the tube voltage of the radiation source 37R used.

As described above, in the grid 29 according to this embodiment, the transmission portion 29A and the absorption portion 29B are alternately arranged in the direction intersecting the movement direction M in which the radiation source 37R is moved. Therefore, according to the grid 29 of this embodiment, in a case in which the tomosynthesis imaging is performed, the scattered rays can be suppressed without being affected by the oblique incidence of the radiation R on the imaging table 30.

The radiation emitting unit 37 comprises the radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. A face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in the up-down direction (Z-axis direction). Further, the arm portion 32 can be rotated with respect to the base 34 by the shaft portion 35. The shaft portion 35 is fixed to the base 34 such that the shaft portion 35 and the arm portion 32 are rotated integrally.

Gears are provided in each of the shaft portion 35 and the compression unit 36. The gears can be switched between an engaged state and a non-engaged state to switch between a state in which the compression unit 36 and the shaft portion 35 are connected and rotated integrally and a state in which the shaft portion 35 is separated from the compression unit 36 and the imaging table 30 and runs idle. In addition, components for switching between the transmission and non-transmission of the power of the shaft portion 35 are not limited to the gears, and various mechanical elements may be used.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

Figure 2C:
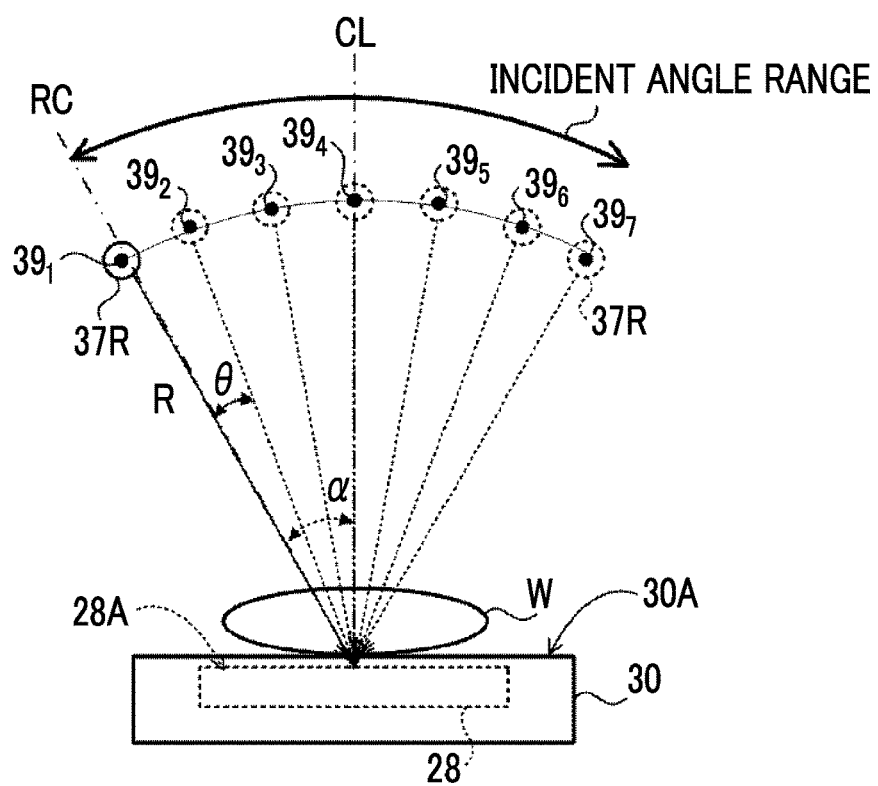
FIG. 2C is a diagram illustrating an example of tomosynthesis imaging.

In a case in which the mammography apparatus 10 performs the tomosynthesis imaging, the radiation source 37R of the radiation emitting unit 37 is moved in the left-right direction of the subject positioned on the imaging table 30. Specifically, the radiation source 37R is continuously moved to each of a plurality of irradiation positions having different irradiation angles by the rotation of the arm portion 32. FIG. 2C is a diagram illustrating an example of the tomosynthesis imaging. In addition, the compression plate 40 is not illustrated in FIG. 2C. In this embodiment, as illustrated in FIG. 2C, the radiation source 37R is moved to a plurality of irradiation positions $39_1$ to $39_7$ having different irradiation angles that are arranged at a predetermined interval of an angle θ. In other words, the radiation source 37R is moved to the positions where the incident angles of the radiation R on the detection surface 28A of the radiation detector 28 are different. In addition, hereinafter, in a case in which the irradiation positions $39_1$ to $39_7$ are generically referred to without being specifically distinguished from each other, they are referred to as irradiation positions 39. Further, in this embodiment, as illustrated in FIG. 2C as an example, the aspect in which the number of irradiation positions is 7 and imaging is performed seven times in the tomosynthesis imaging will be described. However, the irradiation position (irradiation angle) or the number of irradiation positions (the number of imaging operations) in the tomosynthesis imaging is not limited to this embodiment.

At the irradiation positions 39, the radiation R is emitted from the radiation source 37R to a breast W in response to an instruction from the console 12, and the radiation detector 28 captures a radiographic image. In addition, hereinafter, in the tomosynthesis imaging, the radiographic images captured by the radiation detector 28 at a plurality of irradiation positions 39 having different irradiation angles are referred to as "projection images". In a case in which the radiography system 1 performs the tomosynthesis imaging that moves the radiation source 37R to each irradiation position 39 and captures the projection image at each irradiation position 39, seven projection images are obtained. In addition, hereinafter, in a case in which a plurality of types of radiographic images, such as projection images and normal radiographic images which will be described below, are generically referred to, they are simply referred to as "radiographic images".

In addition, as illustrated in FIG. 2C, the incident angle of the radiation R means the angle α formed between a normal line CL to the detection surface 28A of the radiation detector 28 and a radiation axis RC. Further, here, the detection surface 28A of the radiation detector 28 is a surface that is substantially parallel to the imaging surface 30A. Hereinafter, a predetermined range in which the incident angles are different in the tomosynthesis imaging as illustrated in FIG. 2C is referred to as an "incident angle range". A specific example of the incident angle range is a range of ±10 degrees or ±20 degrees with respect to the normal line CL to the detection surface 28A of the radiation detector 28. In this embodiment, the "incident angle" and the "irradiation angle" of the radiation R are synonymous.

On the other hand, in a case in which the mammography apparatus 10 performs the normal imaging, the radiation source 37R of the radiation emitting unit 37 remains at the irradiation position 39 (the irradiation position 39 along the normal direction, the irradiation position $39_4$ in FIG. 2C) where the irradiation angle α is 0 degrees. The radiation R is emitted from the radiation source 37R in response to an instruction from the console 12, and the radiation detector 28 captures a radiographic image. In addition, hereinafter, in some cases, the radiographic image captured by the normal imaging is referred to as a normal radiographic image.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

Figure 3:
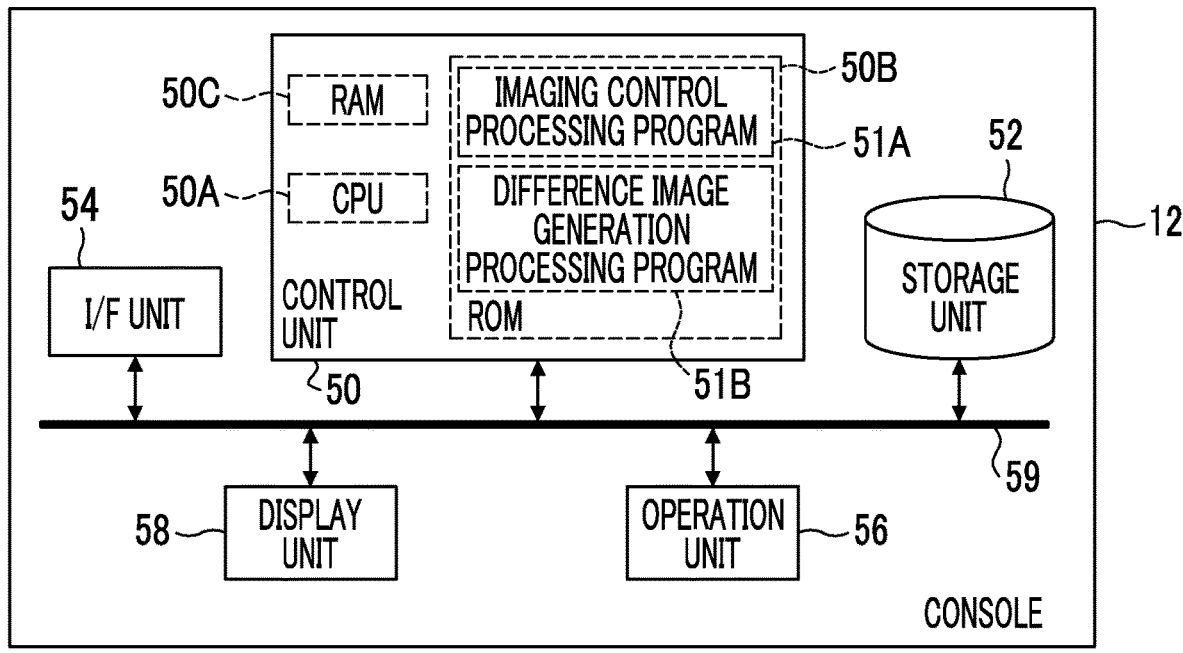
FIG. 3 is a block diagram illustrating an example of the configuration of a console according to the embodiment.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs including an imaging control processing program 51A and a difference image generation processing program 51B, which will be described below, executed by the CPU 50A are stored in the ROM 50B in advance. The RAM 50C temporarily stores various kinds of data. The CPU 50A according to this embodiment is an example of a processor according to the present disclosure. The imaging control processing program 51A according to this embodiment is an example of a control program according to the present disclosure.

For example, the image data of the radiographic image captured by the mammography apparatus 10 and various other kinds of information are stored in the storage unit 52. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
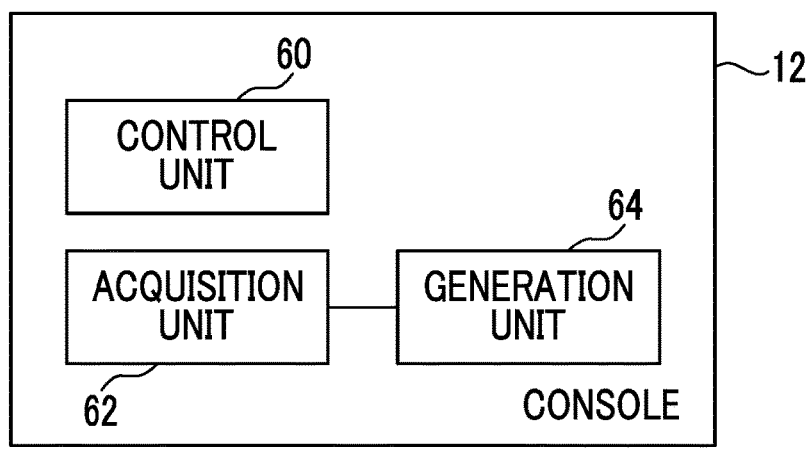
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a control unit 60. For example, in the console 12 according to this embodiment, the CPU 50A of the control unit 50 executes the imaging control processing program 51A stored in the ROM 50B to function as the control unit 60.

The control unit 60 has a function of controlling the contrast imaging and specifically has a function of performing control related to the emission of the radiation R in the contrast imaging by the mammography apparatus 10. The control unit 60 according to this embodiment has a function of continuously performing the normal imaging and the tomosynthesis imaging in a state in which the breast, into which a contrast medium is injected, is compressed by the compression plate 40 in a case in which the contrast imaging is performed.

In the case of the normal imaging, the control unit 60 controls the mammography apparatus 10 such that the radiation R with first energy is emitted from the irradiation position 39 where the irradiation angle is 0 degrees to capture a normal radiographic image.

Further, in the case of the tomosynthesis imaging, the control unit 60 controls the mammography apparatus 10 such that either the radiation R with the first energy or the radiation R with second energy higher than the first energy is emitted at each of the plurality of irradiation positions 39 to capture projection images. Further, in the case of the tomosynthesis imaging, the control unit 60 performs control such that the radiation R with the second energy is emitted at the irradiation position $39_4$ where the irradiation angle is 0 degrees to capture the projection image. In this embodiment, the radiographic image captured by emitting the radiation R with the first energy is referred to as a "low-energy image" and is referred to as a "low-energy projection image" in a case in which the projection images are distinguished. Further, the radiographic image captured by emitting the radiation R with the second energy is referred to as a "high-energy image" and is referred to as a "high-energy projection image" in a case in which the projection images are distinguished.

Specifically, in the case of the tomosynthesis imaging, the control unit 60 performs control such that the low-energy radiation R is emitted at each of the irradiation positions $39_1$, $39_3$, $39_5$, and $39_7$ to capture the low-energy projection images. Further, the control unit 60 performs control such that the high-energy radiation R is emitted at each of the irradiation positions $39_2$, $39_4$, and $39_6$ to capture the high-energy projection images.

For example, an iodine contrast medium having a k-edge of about 33 keV is generally used as the contrast medium used for the contrast imaging. In this case, in the contrast imaging, the radiation R with the first energy lower than the k-edge of the iodine contrast medium is emitted to capture the low-energy image. Further, the radiation R with the second energy higher than the k-edge of the iodine contrast medium is emitted to capture the high-energy image.

Therefore, the control unit 60 according to this embodiment performs control to direct the radiation source 37R to emit the radiation R with the first energy and control to direct the radiation source 37R to emit the radiation R with the second energy in the contrast imaging.

Radiation absorption characteristics are different between the contrast media and the body tissues such as the mammary gland. Therefore, in the high-energy image captured as described above, the body tissues, such as the mammary glands and fat, are shown and the contrast medium is clearly shown. In addition, in the low-energy image, the contrast medium is hardly shown, and the body tissues, such as the mammary glands, are clearly shown. Therefore, a difference image indicating the difference between the low-energy image and the high-energy image can be an image in which a mammary gland structure has been removed and the contrast medium is clearly shown.

Further, as illustrated in FIG. 4, the console 12 according to this embodiment comprises an acquisition unit 62 and a generation unit 64. In the console 12 according to this embodiment, the CPU 50A of the control unit 50 executes the difference image generation processing program 51B stored in the ROM 50B to function as the acquisition unit 62 and the generation unit 64.

The acquisition unit 62 has a function of acquiring the normal radiographic image, the low-energy projection image, and the high-energy projection image captured by the mammography apparatus 10. Specifically, the acquisition unit 62 acquires image data indicating one normal radiographic image, image data indicating each of a plurality of (in this embodiment, four) low-energy projection images, and image data indicating each of a plurality of (in this embodiment, three) high-energy projection images captured by the radiation detector 28 of the mammography apparatus 10 through the I/F unit 24 and the I/F unit 54. The acquisition unit 62 outputs the acquired normal radiographic image, low-energy projection images, and high-energy projection images to the generation unit 64.

The generation unit 64 has a function of generating a plurality of difference images indicating the differences between the low-energy images and the plurality of high-energy images. The generation of the difference images by the generation unit 64 according to this embodiment will be described in detail with reference to FIG. 5. In the normal imaging, the generation unit 64 generates a normal difference image 72 indicating the difference between a high-energy projection image $71H_2$ captured at the irradiation position $39_4$ where the irradiation angle is 0 degrees in the tomosynthesis imaging and a normal radiographic image 70L which is a low-energy image.

Figure 5:
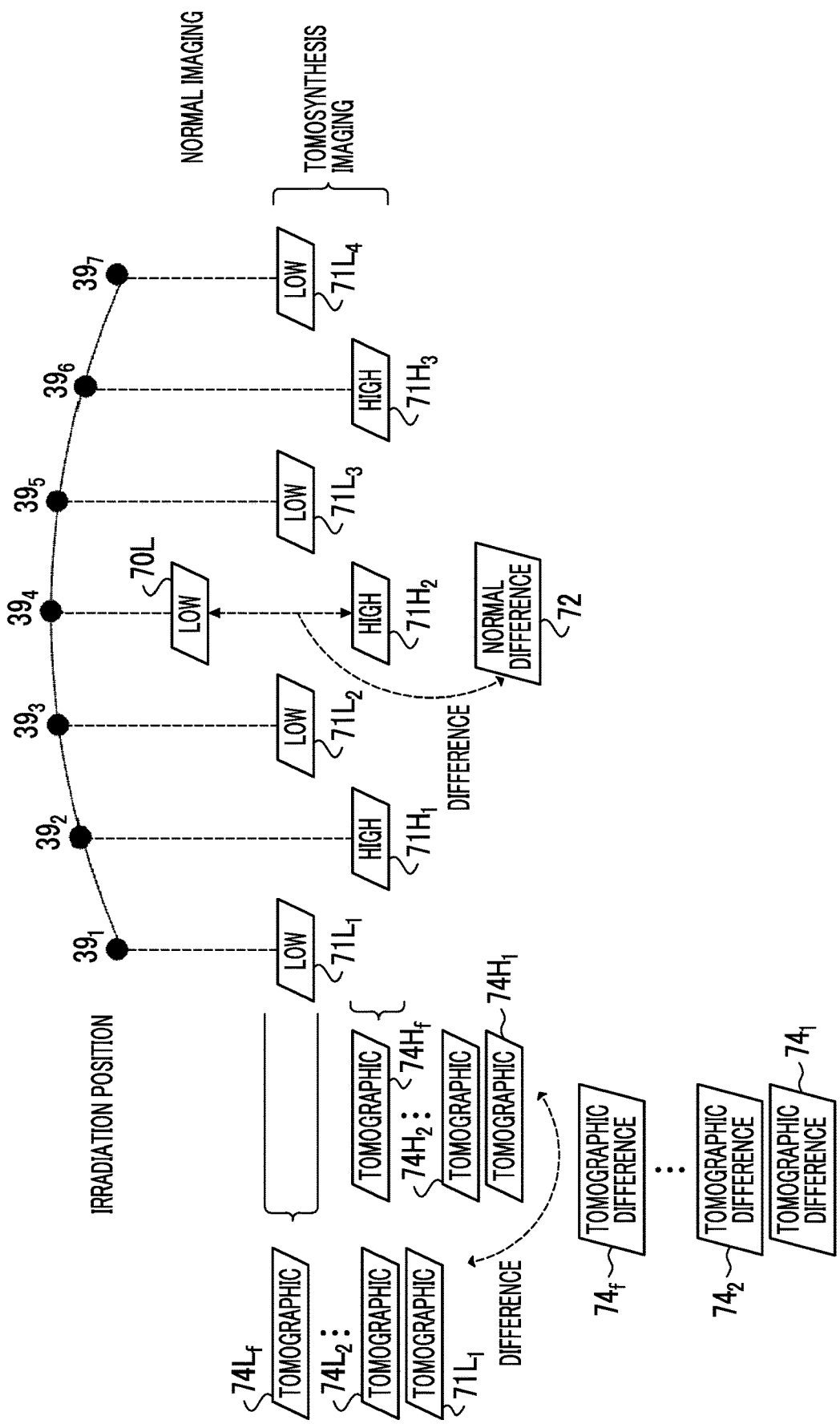
FIG. 5 is a diagram illustrating an example of a method for generating a difference image.

Further, in the tomosynthesis imaging, the generation unit 64 reconstructs low-energy projection images $71L_1$, $71L_2$, $71L_3$, and $71L_4$ to generate a series of low-energy tomographic images 74L with predetermined slice thicknesses. FIG. 5 illustrates an aspect in which f low-energy tomographic images 74L ($74L_1$ to $74L_f$) are generated from a series of low-energy projection images 71L. Further, the generation unit 64 reconstructs the high-energy projection images $71H_1$, $71H_2$, and $71H_3$ to generate a series of high-energy tomographic images 74H having a predetermined slice thickness. FIG. 5 illustrates an aspect in which f high-energy tomographic images 74H (74H$_1$ to 74H$_f$) are generated from a series of high-energy projection images 71H. Then, the generation unit 64 generates tomographic difference images 74 (74$_1$ to 74$_f$) which are difference images indicating the differences between the high-energy tomographic images 74H and the low-energy tomographic images 74L at the corresponding slice positions. In addition, hereinafter, in a case in which the normal difference image and the tomographic difference image are generically referred to without being distinguished from each other, they are referred to as "difference images".

For example, in this embodiment, the difference between the high-energy image and the low-energy image is derived to generate a difference image. Specifically, the generation unit 64 subtracts image data obtained by multiplying the low-energy image by a predetermined coefficient from image data obtained by multiplying the high-energy image by a predetermined coefficient for each corresponding pixel to generate difference image data indicating a difference image in which the mammary gland tissues have been removed and the contrast medium is clearly shown.

Further, a method for generating each of the low-energy tomographic image 74L and the high-energy tomographic image 74H in the generation unit 64 is not particularly limited. For example, reconstruction may be performed by a back projection method, such as a filter back projection (FBP) method or an iterative reconstruction method, or a known technique may be applied. In addition, the slice thicknesses of the low-energy tomographic image 74L and the high-energy tomographic image 74H to be generated may be the same in the two tomographic images, and the specific value of the slice thickness is not limited. The slice thickness can be determined according to, for example, the size of an object of interest, the quality of the radiographic image, the processing load of arithmetic processing in the generation, and an instruction from the user.

Next, the operation of the console 12 in the contrast imaging by the radiography system 1 according to this embodiment will be described with reference to the drawings.

Figure 6:
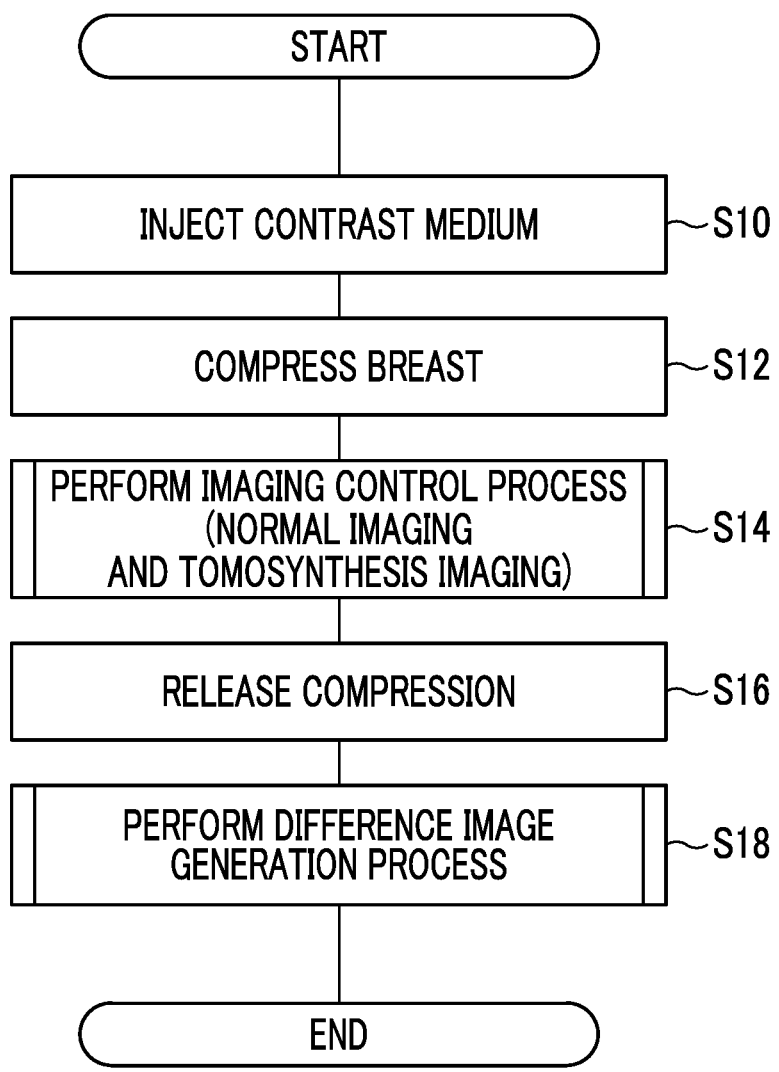
FIG. 6 is a flowchart illustrating an example of the flow of contrast imaging by the radiography system according to the embodiment.

FIG. 6 is a flowchart illustrating an example of the flow of the contrast imaging by the radiography system 1 according to this embodiment. In a case in which the contrast imaging is performed, first, the user injects the contrast medium into the breast as illustrated in Step S10 of FIG. 6. Then, as illustrated in Step S12, the user positions the breast of the subject on the imaging table 30 of the mammography apparatus 10 and compresses the breast with the compression plate 40.

Figure 7:
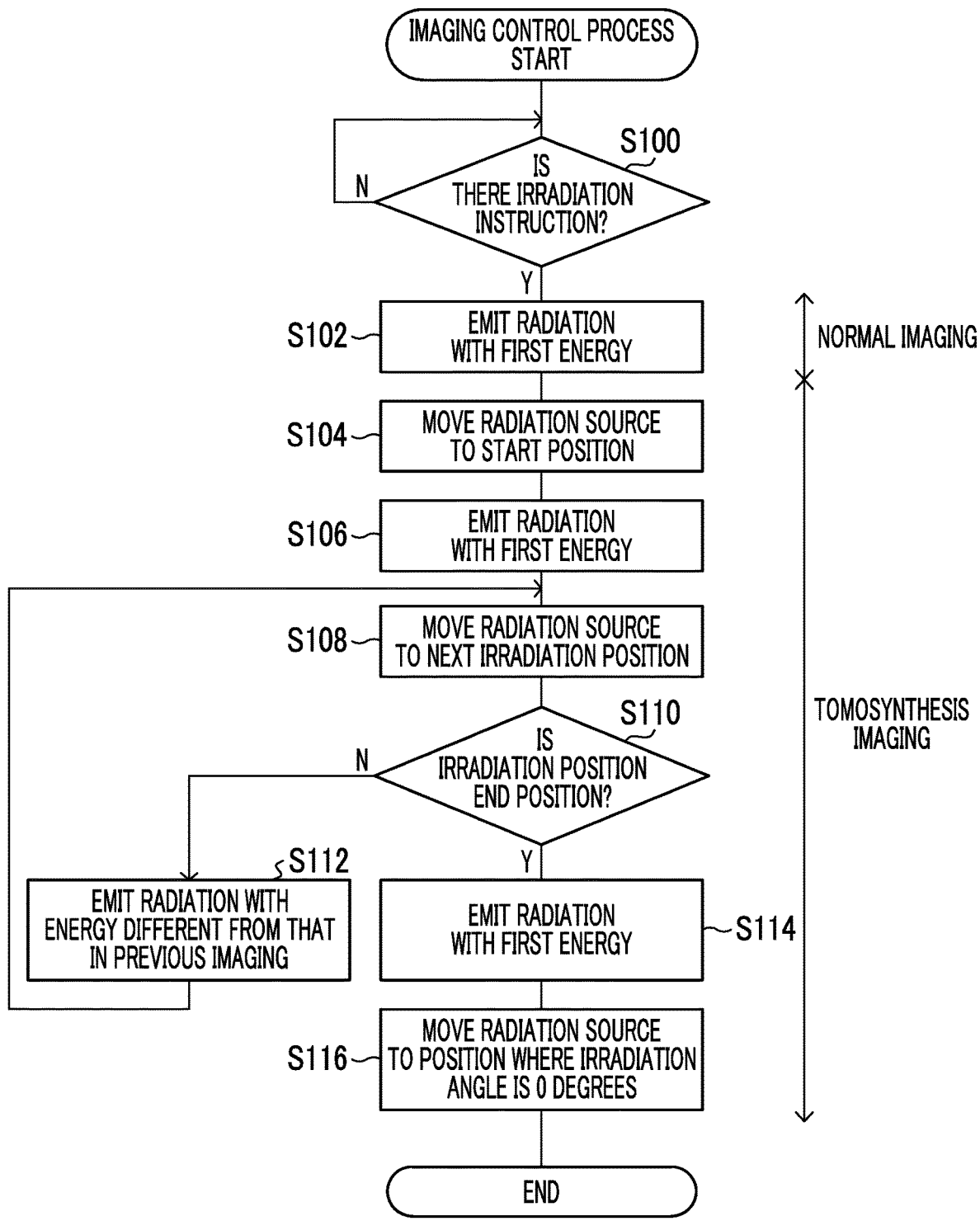
FIG. 7 is a flowchart illustrating an example of the flow of an imaging control process.

Then, in Step S14, the console 12 performs an imaging control process illustrated in FIG. 7 in order to perform the normal imaging and the tomosynthesis imaging in the mammography apparatus 10. In the console 12 according to this embodiment, for example, the CPU 50A of the control unit 50 executes the imaging control processing program 51A stored in the ROM 50B to perform the imaging control process whose example is illustrated in FIG. 7. FIG. 7 is a flowchart illustrating an example of the flow of the imaging control process performed in the console 12 according to this embodiment.

In Step S100 of FIG. 7, the control unit 60 determines whether or not an instruction to emit the radiation R is received. The determination result in Step S100 is "No" until the irradiation instruction is received. On the other hand, in a case in which the irradiation instruction is received, the determination result in Step S100 is "Yes", and the process proceeds to Step S102.

In Step S102, the control unit 60 outputs an instruction to emit the radiation R with the first energy to the mammography apparatus 10. In the mammography apparatus 10, the control unit 20 directs the radiation source 37R to emit the radiation R with the first energy to the breast on the basis of the instruction input from the console 12, and the radiation detector 28 captures a normal radiographic image. In addition, the imaging conditions including the irradiation time of the radiation R may be different between the normal imaging and the tomosynthesis imaging. As such, in a case in which the imaging conditions are different, the control unit 60 also outputs information indicating the imaging conditions for the normal imaging to the mammography apparatus 10 in this step. As such, the normal imaging is performed in the mammography apparatus 10 by the process in this step.

Then, in Step S104, the control unit 60 moves the radiation source 37R to the irradiation position 39$_1$ which is a start position where the emission of the radiation R is started.

Then, in Step S106, the control unit 60 outputs an instruction to emit the radiation R with the first energy to the mammography apparatus 10 as in Step S102. In the mammography apparatus 10, the control unit 20 directs the radiation source 37R to emit the radiation R with the first energy to the breast on the basis of the instruction input from the console 12, and the radiation detector 28 captures a low-energy projection image.

Then, in Step S108, the control unit 60 moves the radiation source 37R to the next irradiation position 39. Then, in Step S110, the control unit 60 determines whether or not the irradiation position 39 to which the radiation source 37R has been moved is the irradiation position 39$_7$ which is an end position where the emission of the radiation R ends. In a case in which the position of the radiation source 37R is not the irradiation position 39$_7$, the determination result in Step S110 is "No", and the process proceeds to Step S112.

In Step S112, the control unit 60 outputs an instruction to emit the radiation R having energy different from that in the previous imaging operation to the mammography apparatus 10. Specifically, in a case in which the radiation with the first energy is emitted to capture the low-energy projection image in the previous capture of the projection image, an instruction to emit the radiation R with the second energy is output to the mammography apparatus 10. In the mammography apparatus 10, the control unit 20 directs the radiation source 37R to emit the radiation R with the second energy to the breast on the basis of the instruction input from the console 12, and the radiation detector 28 captures a high-energy projection image. Further, in a case in which the radiation with the second energy is emitted to capture a high-energy projection image in the previous capture of the projection image, an instruction to emit the radiation R with the first energy is output to the mammography apparatus 10. In the mammography apparatus 10, the control unit 20 directs the radiation source 37R to emit the radiation R with the first energy to the breast on the basis of the instruction input from the console 12, and the radiation detector 28 captures a low-energy projection image.

In a case in which the process in Step S112 ends, the process returns to Step S108, and the processes in Steps S108 and S110 are repeated.

On the other hand, in a case in which the position of the radiation source 37R is the irradiation position 39$_7$, the determination result in Step S110 is "Yes", and the process proceeds to Step S114. In Step S114, the control unit 60 outputs an instruction to emit the radiation R with the first energy to the mammography apparatus 10 as in Step S102.

In the mammography apparatus 10, the control unit 20 directs the radiation source 37R to emit the radiation R with the first energy to the breast on the basis of the instruction input from the console 12, and the radiation detector 28 captures a low-energy projection image.

Then, in Step S116, the control unit 60 moves the radiation source 37R to the irradiation position $39_4$ where the irradiation angle α is 0 degrees. As such, the tomosynthesis imaging is performed in the mammography apparatus 10 by the processes in Steps S104 to S116. In a case in which the process in Step S116 ends, the imaging control process illustrated in FIG. 7 ends.

In a case in which the imaging control process illustrated in FIG. 7 ends in this way, the contrast imaging ends, and the process in Step S14 illustrated in FIG. 6 ends.

Since the contrast imaging ends, the user releases the compression of the breast by the compression plate 40 as illustrated in the next Step S16.

Figure 8:
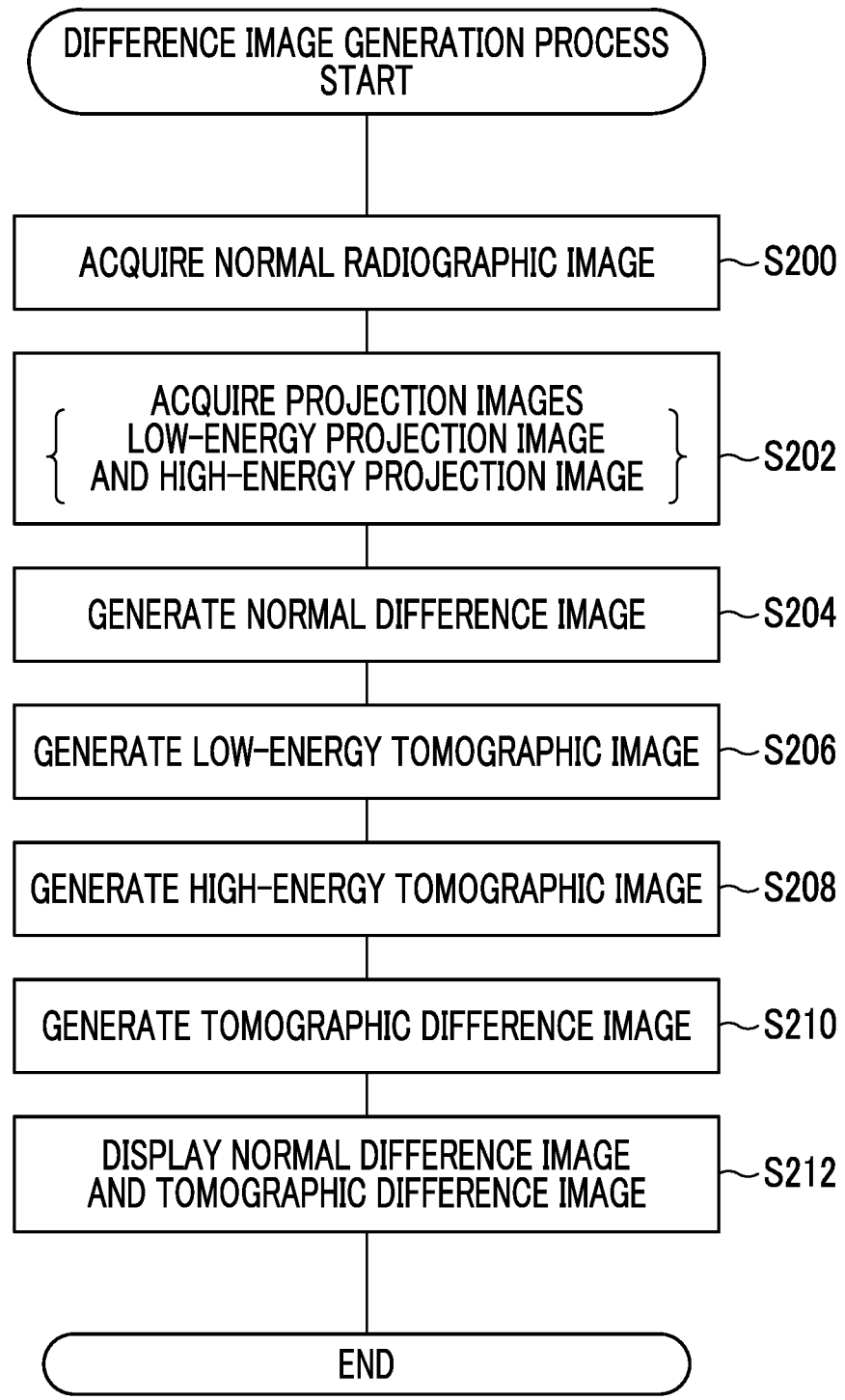
FIG. 8 is a flowchart illustrating an example of the flow of a difference image generation process.

Then, in Step S18, the console 12 performs a difference image generation process illustrated in FIG. 8. In the console 12 according to this embodiment, for example, the CPU 50A of the control unit 50 executes the difference image generation processing program 51B stored in the ROM 50B to perform the difference image generation process whose example is illustrated in FIG. 8. FIG. 8 is a flowchart illustrating an example of the flow of the difference image generation process performed in the console 12 according to this embodiment.

In Step S200, the acquisition unit 62 acquires the normal radiographic image captured by the normal imaging from the mammography apparatus 10 as described above. Then, in Step S202, the acquisition unit 62 acquires the low-energy projection image and the high-energy projection image captured by the tomosynthesis imaging. In addition, the timing when the acquisition unit 62 acquires the normal radiographic image, the low-energy projection image, and the high-energy projection image is not limited. For example, whenever each of the normal radiographic image, the low-energy projection image, and the high-energy projection image is captured, the normal radiographic image, the low-energy projection image, and the high-energy projection image may be acquired from the mammography apparatus 10. Further, for example, after the normal imaging and the tomosynthesis imaging end, the normal radiographic image, the low-energy projection image, and the high-energy projection image stored in the storage unit 22 of the mammography apparatus 10 may be acquired. Furthermore, the order in which the normal radiographic image, the low-energy projection image, and the high-energy projection image are acquired is not limited.

Then, in Step S204, the generation unit 64 generates a normal difference image as described above. Specifically, the generation unit 64 generates the normal difference image (see the normal difference image 72 in FIG. 5) indicating the difference between the high-energy projection image (see the high-energy projection image $71H_2$ in FIG. 5) captured at the irradiation position $39_4$ where the irradiation angle is 0 degrees among the high-energy projection images acquired in Step S202 and the normal radiographic image (see the normal radiographic image 70L in FIG. 5) acquired in Step S200.

Then, in Step S206, the generation unit 64 generates a low-energy tomographic image as described above. Specifically, the generation unit 64 reconstructs the low-energy projection images (see the low-energy projection images $71L_1$ to $71L_4$ in FIG. 5) acquired in Step S202 to generate the low-energy tomographic images $74L_1$ to $74L_f$.

Then, in Step S208, the generation unit 64 generates a high-energy tomographic image as described above. Specifically, the generation unit 64 reconstructs the high-energy projection images (see the high-energy projection images $71H_1$ to $71H_3$ in FIG. 5) acquired in Step S202 to generate the high-energy tomographic images $74H_1$ to $74H_f$.

Then, in Step S210, the generation unit 64 generates a tomographic difference image as described above. Specifically, the generation unit 64 generates the tomographic difference images (see the tomographic difference images $74_1$ to $74_f$ in FIG. 5) indicating the differences between the high-energy tomographic images (see the high-energy tomographic images $74H_1$ to $74H_f$ in FIG. 5) generated in Step S208 and the low-energy tomographic images (see the low-energy tomographic images $74L_1$ to $74L_f$ in FIG. 5) generated in Step S206.

Then, in Step S212, the generation unit 64 displays, on the display unit 58, the normal difference image generated in the Step S204 and the tomographic difference images generated in the Step S210 as described above. For example, the generation unit 64 according to this embodiment displays, on the display unit 58, the normal difference image and the tomographic difference images subjected to a gradation enhancement process, a frequency enhancement processing, or the like. In a case in which the process in Step S212 ends, the difference image generation process illustrated in FIG. 8 ends.

In a case in which the difference image generation process illustrated in FIG. 8 ends in this way, the difference image generation process in Step S18 illustrated in FIG. 6 ends. Therefore, a series of processes related to the contrast imaging in the radiography system 1 according to this embodiment ends. In addition, the normal radiographic image, the low-energy projection image, and the high-energy projection image captured by the mammography apparatus 10 according to this embodiment and the normal difference image, the low-energy tomographic image, the high-energy tomographic image, and the tomographic difference image generated by the console 12 may be stored in, for example, the storage unit 52 of the console 12 or a picture archiving and communication system (PACS).

As described above, the console 12 according to the above-described embodiment comprises the CPU 50A as at least one processor. The CPU 50A controls the mammography apparatus 10 that irradiates the breast, into the contrast medium is injected and which is compressed by the compression plate 40, with the radiation R from the radiation source 37R to capture a radiographic image of the breast such that the normal imaging and the tomosynthesis imaging are performed in a state in which the breast is compressed by the compression plate 40. In addition, in the normal imaging, the CPU 50A performs control such that the radiation R with the first energy is emitted from the irradiation position $39_4$ where the irradiation angle is 0 degrees to capture a normal radiographic image. Further, in the tomosynthesis imaging, the CPU 50A performs control such that the radiation R with either the first energy or the second energy higher than the first energy is emitted at each of a plurality of irradiation positions 39 having different irradiation angles and the radiation R with the second energy is emitted at the irradiation position $39_4$ where the irradiation angle is 0 degrees to capture a plurality of low-energy projection images based on the radiation R with the first energy and a plurality of high-energy projection images based on the radiation R with the second energy.

As such, the console 12 according to this embodiment performs control such that the radiation R with the first energy is emitted to capture the normal radiographic image in the normal imaging and the radiation R with the second energy is emitted at the irradiation position $39_4$ where the irradiation angle is 0 degrees to capture the high-energy projection image in the tomosynthesis imaging. This configuration makes it possible to generate the normal difference image from the normal radiographic image and the high-energy projection image in a case in which the irradiation angle is 0 degrees. Therefore, according to the console 12 of this embodiment, it is possible to obtain the normal difference image without capturing both the low-energy image and the high-energy image in the normal imaging. As a result, according to the console 12 of this embodiment, it is possible to reduce the overall time of the contrast imaging in which the normal imaging and the tomosynthesis imaging are continuously performed.

Figure 9:
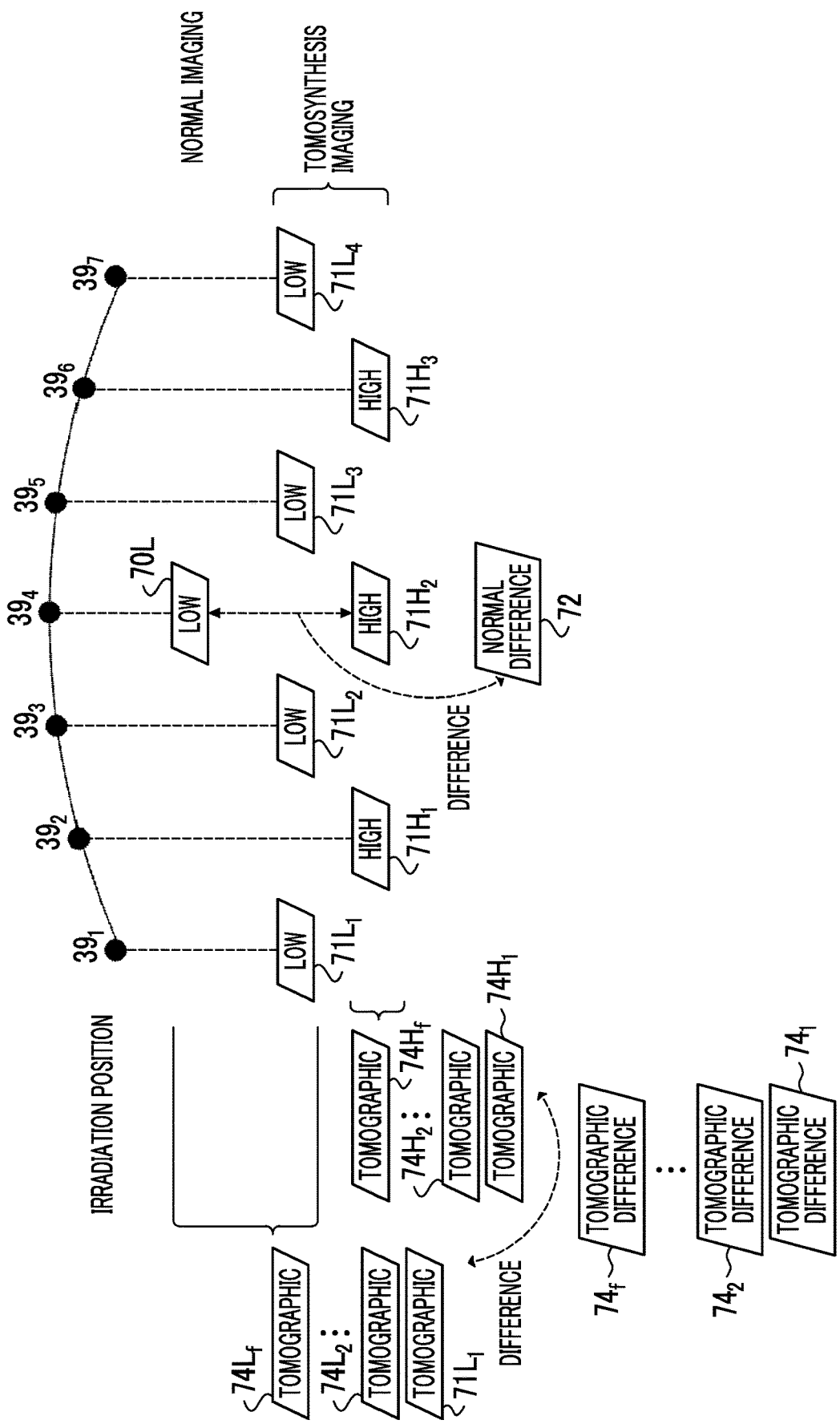
FIG. 9 is a diagram illustrating another example of the method for generating the difference image.

In the above-described embodiment, the aspect in which the low-energy tomographic image is generated using only the low-energy projection image captured by the tomosynthesis imaging has been described. However, as illustrated in FIG. 9, the low-energy tomographic image may be generated from the normal radiographic image captured by the normal imaging and the low-energy projection image captured by the tomosynthesis imaging. In the example illustrated in FIG. 9, the generation unit 64 reconstructs the normal radiographic image 70L and the low-energy projection images $71L_1$ to $71L_4$ to generate a series of low-energy tomographic images $74L_1$ to $74L_f$ having a predetermined slice thickness. In addition, in a case in which the imaging conditions including the irradiation time of the radiation R are different between the normal imaging and the tomosynthesis imaging as described above, for example, the normal radiographic image may be multiplied by a coefficient corresponding to the imaging conditions and then used to reconstruct the low-energy tomographic image.

In addition, in the above-described embodiment, the imaging conditions at each irradiation position 39 are the same in the tomosynthesis imaging. However, the imaging conditions may vary depending on the irradiation position 39. For example, the dose of the radiation R emitted at the irradiation position $39_4$ where the irradiation angle is 0 degrees may be higher than the dose of the radiation R emitted from other irradiation positions 39. In this case, it is possible to improve the quality of the normal difference image.

Further, in the above-described embodiment, the aspect in which the radiation R with the first energy is emitted at the irradiation position $39_1$ which is the start position in the tomosynthesis imaging has been described. However, the energy of the radiation R emitted at the start position may vary depending on, for example, the number of irradiation positions 39. For example, in a case in which the radiation R with the first energy and the radiation R with the second energy are alternately emitted and the total number of irradiation positions 39 is 3+4×j (j=1, 2, 3, . . . ), the radiation R with the first energy is emitted at the irradiation position $39_1$ which is the start position. Further, for example, in a case in which the radiation R with the first energy and the radiation R with the second energy are alternately emitted and the total number of irradiation positions 39 is 1+4×m (m=1, 2, 3, . . . ), the radiation R with the second energy is emitted at the irradiation position $39_1$ which is the start position. In a case in which the radiation R with the first energy and the radiation R with the second energy are alternately emitted at each irradiation position 39 in odd-numbered tomosynthesis imaging operations, the energy of the radiation emitted at the start position is appropriately set according to the number of times the radiation is emitted, which makes it possible to acquire projection images which are symmetric with respect to the normal line CL as the axis and to emit the radiation R with the second energy at the irradiation position $39_4$ where the irradiation angle is 0 degrees.

Figure 10:
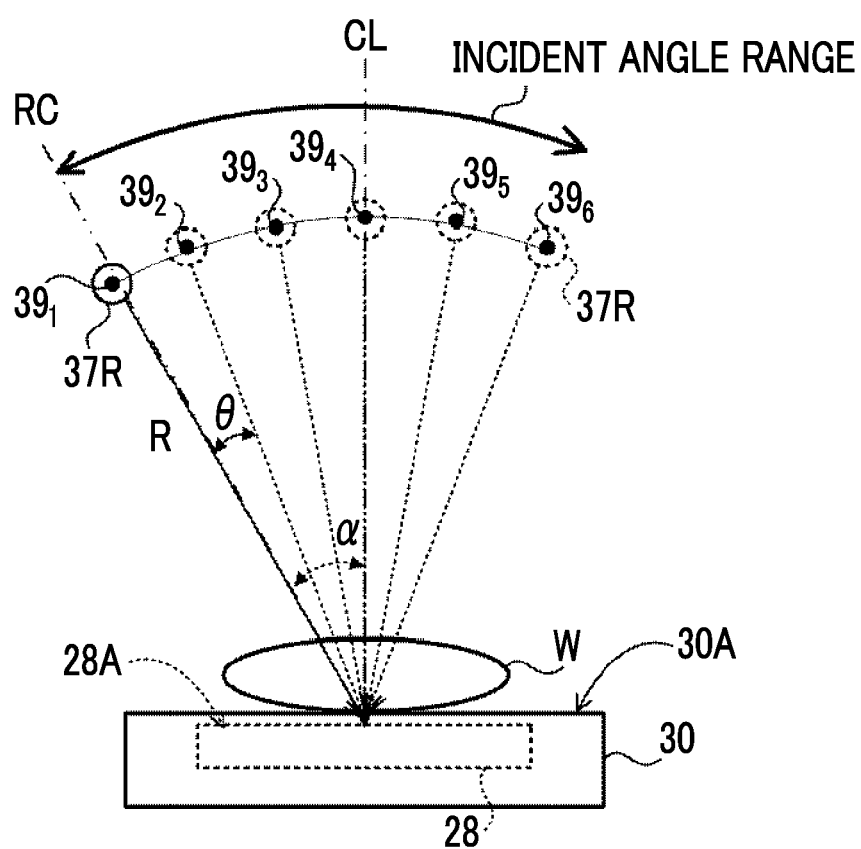
FIG. 10 is a diagram illustrating another example of the tomosynthesis imaging.

Further, in the above-described embodiment, the aspect in which the number of times the projection image is captured in the tomosynthesis imaging, specifically, the sum of the number of times the low-energy projection image is captured and the number of times the high-energy projection image is captured is an odd number. However, the sum may be an even number. In this case, the number of times the low-energy projection image is captured and the number of times the high-energy projection image is captured may be equal to each other. For example, in the example illustrated in FIG. 10, the radiation R with the first energy is emitted at the irradiation positions $39_1$, $39_3$, and $39_5$ to capture the low-energy projection images, and the radiation R with the second energy is emitted at the irradiation positions $39_2$, $39_4$, and $39_6$ to capture the high-energy projection images. In this embodiment, the radiation R with the second energy can also be emitted at the irradiation position $39_4$ where the irradiation angle is 0 degrees.

Further, in the above-described embodiment, the aspect in which the normal imaging is performed before the tomosynthesis imaging has been described. However, the tomosynthesis imaging may be performed before the normal imaging. In addition, since the normal imaging is performed first, it is possible to detect, for example, the dose of the radiation emitted to the radiation detector 28 from the normal radiographic image obtained by the normal imaging.

Furthermore, in the above-described embodiment, after the imaging control process which is the process in Step S14 in FIG. 6, that is, the contrast imaging ends, the difference image generation process is performed. However, the timing when the difference image generation process is performed, that is, the timing when the difference image is generated or displayed is not limited to this aspect. For example, each of the generation of the difference image and the display of the difference image may be performed at the time the user wants after the contrast imaging.

Moreover, in the above-described embodiment, the aspect in which the radiation R is emitted at each irradiation position 39 after the movement of the radiation source 37R is stopped has been described. However, the radiation R may be emitted at each irradiation position 39 while the radiation source 37R is being moved. In other words, the tomosynthesis imaging may be performed without stopping the radiation source 37R from the start position to the end position.

In addition, the grid included in the mammography apparatus 10 is not limited to the grid 29 in the above-described embodiment. For example, a grid in which the transmission portion 29A and the absorption portion 29B are disposed in the imaging table 30 while extending in the front-rear direction of the subject positioned on the imaging table 30 may be applied. In other words, a grid obtained by rotating the grid 29 according to this embodiment by 90 degrees may be applied. In this case, a retraction mechanism that retracts the grid from the inside of the detection surface of the radiation detector 28 to the outside of the detection surface may be provided. In a case in which two-dimensional imaging, such as the normal imaging, is performed, the grid may be inserted into the detection surface of the radiation detector 28. In a case in which the tomosynthesis imaging is performed, the grid may be retracted to the outside of the detection surface of the radiation detector 28.

Further, in the above-described embodiment, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the control unit 60, the acquisition unit 62, and the generation unit 64.

Furthermore, in the above-described embodiment, for example, the following various processors can be used as the hardware structure of processing units performing various processes such as the control unit 60, the acquisition unit 62, and the generation unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging control processing program 51A and the difference image generation processing program 51B are stored (installed) in the ROM 50B in advance has been described. However, the present disclosure is not limited thereto. The imaging control processing program 51A and the difference image generation processing program 51B may be recorded on a recording medium, such as a compact disc read only memory (CD-ROM), a digital versatile disc read only memory (DVD-ROM), or a universal serial bus (USB) memory, and then provided. Further, each of the imaging control processing program 51A and the difference image generation processing program 51B may be downloaded from an external device through a network.

What is claimed is:

1. A control device comprising:
   at least one processor,
   wherein the processor controls a mammography apparatus that irradiates a breast, into which a contrast medium is injected and which is compressed by a compression member, with radiation from a radiation source to capture a radiographic image of the breast, such that normal imaging, which emits the radiation with first energy from an irradiation position where an irradiation angle is 0 degrees to capture a normal radiographic image, and tomosynthesis imaging, which emits the radiation with either the first energy or second energy higher than the first energy at each of a plurality of irradiation positions having different irradiation angles, are performed; and
   wherein, during a single compression of a breast by the compression member:
      the normal imaging emits the radiation with first energy from an irradiation position where an irradiation angle is 0 degrees,
      the tomosynthesis imaging emits the radiation with the second energy at an irradiation position where the irradiation angle is 0 degrees,
      the tomosynthesis imaging emits the radiation with either the first energy or second energy at each of a plurality of irradiation positions excluding the irradiation position where the irradiation angle is 0 degrees, to capture a plurality of low-energy projection images based on the radiation with the first energy and a plurality of high-energy projection images based on the radiation with the second energy are performed, and
      a low energy projection image by the normal imaging and a high energy projection image by the tomosynthesis imaging are captured at the irradiation position where the irradiation angle is 0 degrees, in a state in which the breast is compressed by the compression member.

2. The control device according to claim 1,
   wherein the processor acquires the normal radiographic image, the plurality of low-energy projection images, and the plurality of high-energy projection images, generates a difference image indicating a difference between the high-energy projection image in a case in which the irradiation angle is 0 degrees among the plurality of high-energy projection images and the normal radiographic image, and generates tomographic difference images indicating differences between high-energy tomographic images generated by reconstructing the plurality of high-energy projection images and low-energy tomographic images generated by reconstructing the plurality of low-energy projection images.

3. The control device according to claim 1,
   wherein the processor acquires the normal radiographic image, the plurality of low-energy projection images, and the plurality of high-energy projection images, generates a difference image indicating a difference between the high-energy projection image in a case in which the irradiation angle is 0 degrees among the plurality of high-energy projection images and the normal radiographic image, and generates tomographic difference images indicating differences between high-energy tomographic images generated by reconstructing the plurality of high-energy projection images and low-energy tomographic images generated by reconstructing the normal radiographic image and the plurality of low-energy projection images.

4. The control device according to claim 1,
wherein a sum of the number of times the low-energy projection image is captured and the number of times the high-energy projection image is captured is an odd number.

5. The control device according to claim 1,
wherein the number of times the low-energy projection image is captured is equal to the number of times the high-energy projection image is captured.

6. The control device according to claim 1,
wherein the processor performs control such that a dose of the radiation emitted from the irradiation position where the irradiation angle is 0 degrees in the tomosynthesis imaging is higher than a dose of the radiation emitted from the irradiation positions having other irradiation angles.

7. The control device according to claim 1,
wherein the processor performs control such that the normal imaging is performed before the tomosynthesis imaging.

8. The control device according to claim 1,
wherein the irradiation position where the irradiation angle is 0 degrees is an irradiation position along a normal direction to an imaging table on which the breast is positioned.

9. The control device according to claim 1,
wherein the mammography apparatus comprises a grid in which a transmission portion that transmits the radiation and an absorption portion that absorbs the radiation are alternately arranged in a direction intersecting a movement direction in which the radiation source emitting the radiation is moved in the tomosynthesis imaging.

10. A control method comprising:
controlling a mammography apparatus that irradiates a breast, into which a contrast medium is injected and which is compressed by a compression member, with radiation from a radiation source to capture a radiographic image of the breast such that normal imaging, which emits the radiation with first energy from an irradiation position where an irradiation angle is 0 degrees to capture a normal radiographic image, and tomosynthesis imaging, which emits the radiation with either the first energy or second energy higher than the first energy at each of a plurality of irradiation positions having different irradiation angles, are performed,
wherein, during a single compression of a breast by the compression member:
the normal imaging emits the radiation with first energy from an irradiation position where an irradiation angle is 0 degrees,
the tomosynthesis imaging emits the radiation with the second energy at the irradiation position where the irradiation angle is 0 degrees,
the tomosynthesis imaging emits the radiation with either the first energy or second energy at each of a plurality of irradiation positions excluding the irradiation position where the irradiation angle is 0 degrees, to capture a plurality of low-energy projection images based on the radiation with the first energy and a plurality of high-energy projection images based on the radiation with the second energy are performed, and
a low energy projection image by the normal imaging and a high energy projection image by the tomosynthesis imaging are captured at the irradiation position where the irradiation angle is 0 degrees, in a state in which the breast is compressed by the compression member.

11. A non-transitory computer-readable storage medium storing a control program that causes a computer to perform a process of:
controlling a mammography apparatus that irradiates a breast, into which a contrast medium is injected and which is compressed by a compression member, with radiation from a radiation source to capture a radiographic image of the breast such that normal imaging, which emits the radiation with first energy from an irradiation position where an irradiation angle is 0 degrees to capture a normal radiographic image, and tomosynthesis imaging, which emits the radiation with either the first energy or second energy higher than the first energy at each of a plurality of irradiation positions having different irradiation angles, are performed,
wherein, during a single compression of a breast by the compression member:
the normal imaging emits the radiation with first energy from an irradiation position where an irradiation angle is 0 degrees,
the tomosynthesis imaging emits the radiation with the second energy at the irradiation position where the irradiation angle is 0 degrees,
the tomosynthesis imaging emits the radiation with either the first energy or second energy at each of a plurality of irradiation positions excluding the irradiation position where the irradiation angle is 0 degrees, to capture a plurality of low-energy projection images based on the radiation with the first energy and a plurality of high-energy projection images based on the radiation with the second energy are performed, and
a low energy projection image by the normal imaging and a high energy projection image by the tomosynthesis imaging are captured at the irradiation position where the irradiation angle is 0 degrees, in a state in which the breast is compressed by the compression member.

* * * * *